(12) United States Patent
Miyazawa

(10) Patent No.: US 9,790,241 B2
(45) Date of Patent: Oct. 17, 2017

(54) REAGENT FOR ENHANCING GENERATION OF CHEMICAL SPECIES

(71) Applicant: TOYO GOSEI CO., LTD., Ichikawa-shi, Chiba (JP)

(72) Inventor: Takashi Miyazawa, Ichikawa (JP)

(73) Assignees: Toyo Goesi Co., Ltd., Ichikawa-shi, Chiba (JP); Osaka University, Suita-shi, Osaka (JP)

(*) Notice: Subject to any disclaimer, the term of this patent is extended or adjusted under 35 U.S.C. 154(b) by 0 days.

(21) Appl. No.: 14/392,316

(22) PCT Filed: Jun. 27, 2014

(86) PCT No.: PCT/JP2014/003451
§ 371 (c)(1),
(2) Date: Dec. 24, 2015

(87) PCT Pub. No.: WO2014/208104
PCT Pub. Date: Dec. 31, 2014

(65) Prior Publication Data
US 2016/0145274 A1 May 26, 2016

Related U.S. Application Data

(60) Provisional application No. 61/957,269, filed on Jun. 27, 2013.

(51) Int. Cl.
| | | |
|---|---|---|
| *G03F 7/004* | (2006.01) |
| *C07F 7/08* | (2006.01) |
| *C07F 7/22* | (2006.01) |
| *C07F 7/30* | (2006.01) |
| *G03F 7/039* | (2006.01) |
| *G03F 7/20* | (2006.01) |

(52) U.S. Cl.
CPC ............ *C07F 7/0818* (2013.01); *C07F 7/22* (2013.01); *C07F 7/30* (2013.01); *G03F 7/0045* (2013.01); *G03F 7/0046* (2013.01); *G03F 7/0397* (2013.01); *G03F 7/203* (2013.01)

(58) Field of Classification Search
CPC .. C07F 7/0818; C07F 7/22; C07F 7/30; G03F 7/004
USPC .......................................... 430/270.1; 585/26
See application file for complete search history.

(56) References Cited

U.S. PATENT DOCUMENTS

| 6,171,755 B1 | 1/2001 | Elian et al. |
| 7,851,252 B2 | 12/2010 | Nealey et al. |
| 9,228,949 B2 * | 1/2016 | Tang .................. G01N 21/643 |

(Continued)

FOREIGN PATENT DOCUMENTS

| JP | 4165359 | 6/1992 |
| JP | 04274242 A * | 9/1992 |

(Continued)

OTHER PUBLICATIONS

Schreivogel et al, "Synthesis and Redox Behavior of Novel 9,10-Diphenylphenanthrenes", Helevetica Chimica Acta, vol. 93, 1912-1924 (2010).*

(Continued)

*Primary Examiner* — Amanda C Walke
(74) *Attorney, Agent, or Firm* — TraskBritt, P.C.

(57) ABSTRACT

A reagent that enhances acid generation of a photoacid generator and composition containing such reagent is disclosed.

3 Claims, 1 Drawing Sheet

(56) References Cited

U.S. PATENT DOCUMENTS

| | | | |
|---|---|---|---|
| 9,240,565 B2 | 1/2016 | Osaki et al. | |
| 2006/0287465 A1* | 12/2006 | Suzuki | C08G 59/683 |
| | | | 528/98 |
| 2013/0071789 A1 | 3/2013 | Iwashita et al. | |
| 2013/0115554 A1 | 5/2013 | Takaki et al. | |
| 2013/0210047 A1* | 8/2013 | Tang | C07D 207/448 |
| | | | 435/18 |
| 2015/0060728 A1 | 3/2015 | Enomoto et al. | |
| 2015/0141687 A1 | 5/2015 | Miyazawa | |
| 2015/0274871 A1 | 10/2015 | Osaki et al. | |

FOREIGN PATENT DOCUMENTS

| | | |
|---|---|---|
| JP | 06059447 A * | 3/1994 |
| JP | 11-231542 | 8/1999 |
| JP | 2002-311586 | 10/2002 |
| JP | 2010-151999 | 7/2010 |
| JP | 2011227492 A * | 11/2011 |
| JP | 2013-031125 | 2/2013 |
| JP | 2013068646 | 4/2013 |
| JP | 2013101277 | 5/2013 |
| JP | 2013-211479 | 10/2013 |
| WO | 2004012012 | 2/2004 |
| WO | 2014129556 | 8/2014 |
| WO | 2014208104 | 12/2014 |

OTHER PUBLICATIONS

Translation of JP 2011227492 (no date).*
Seiji Nagahara et al., Methods to Improve Radiation Sensitivity an Chemically Amplified Resists by Using Chain Reactions of Acid Generation, Advances in Resist Technology and Processing XVII, 2000, pp. 386-394, vol. 3999, Proceedings of SPIE.
PCT International Search Report dated Sep. 30, 2014, PCT/JP2014/003451.
John J. Eisch et al., 1,n-Triorganosilyl Migrations in the Rearrangements of Silyl-Substituted Organolithium Compounds, Journal of Organometallic Chemistry, 1982, pp. 5-23, vol. 225, Elsevier Sequoia S.A.
PCT Written Opinion dated Sep. 30, 2014, PCT/JP2014/003451.
Application for U.S. Appl. No. 14/392,350, sharing common inventors, available on the U.S. Patent Office website.
Application for U.S. Appl. No. 14/915,496, sharing common inventors, available on the U.S. Patent Office website.
Application for U.S. Appl. No. 15/027,855, sharing common inventors, available on the U.S. Patent Office website.

* cited by examiner

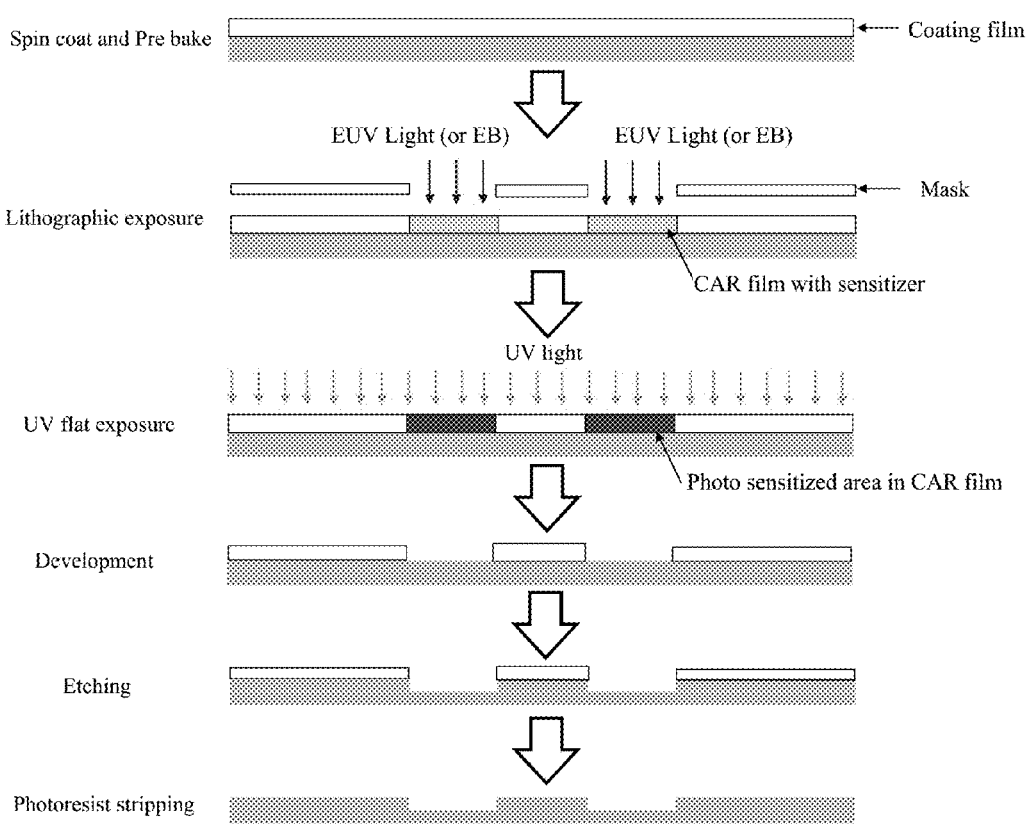

REAGENT FOR ENHANCING GENERATION OF CHEMICAL SPECIES

CROSS-REFERENCE TO RELATED APPLICATIONS

This application is a national phase entry under 35 U.S.C. §371 of International Patent Application PCT/JP2014/003451, filed Jun. 27, 2014, designating the United States of America and published in English as International Patent Publication WO 2014/208104 A1 on Dec. 31, 2014, which claims the benefit under Article 8 of the Patent Cooperation Treaty and under 35 U.S.C. §119(e) to U.S. Provisional Patent Application Ser. No. 61/957,269, filed Jun. 27, 2013, the disclosure of which is hereby incorporated herein in its entirety by this reference.

TECHNICAL FIELD

Several aspects of this disclosure relate to the fields of a reagent enhancing a generation of a chemical species such as an acid and base. An intermediate formed from the reagent functions as a photosensitizer, which also enhances a chemical species.

BACKGROUND

Current high-resolution lithographic processes are based on chemically amplified resists (CARs) and are used to pattern features with dimensions less than 100 nm.

A method for forming pattern features with dimensions less than 100 nm is disclosed in U.S. Pat. No. 7,851,252 (filed on Feb. 17, 2009), the contents of the entirety of which are incorporated herein by this reference.

BRIEF SUMMARY

A reagent relating to an aspect of the disclosure, wherein the reagent is capable of generating an intermediate, and a product is capable of being formed from the intermediate by elimination of an elimination group.

A reagent relating to an aspect of this disclosure, wherein the reagent is capable of generating a product accompanied with the formation of a multiple bond between a first atom and a second atom and the elimination of an elimination group bonded to the second atom; and wherein the second atom is not an oxygen atom.

A reagent relating to an aspect of the disclosure, wherein the reagent is capable of generating a product accompanied with the formation of a multiple bond between a first atom and a second atom and the elimination of an elimination group bonded to the second atom; and wherein the second atom is an atom of an element of group 14.

A composition relating to an aspect of this disclosure includes any one of the above reagents and a precursor that generates a chemical species enhanced by the reagent.

With regard to the composition, it is preferred that the composition further includes a polymer that is capable of reacting with the chemical species.

With regard to the composition, it is preferred that the chemical species is an acid or base.

A method for manufacturing a device relating to an aspect of the disclosure, wherein the method uses any one of the above compositions.

A method for manufacturing a device relating to an aspect of this disclosure includes applying a solution of any one of the above compositions to a substrate, such that a coating film including the composition is formed on the substrate; a first exposure of the coating film to at least one of a first electromagnetic ray and a first particle ray, such that a first portion of the coating film is irradiated with the at least one of the first electromagnetic ray and the first particle ray while a second portion of the coating film is not irradiated with the at least one of the first electromagnetic ray and the first particle ray; and a second exposure of the coating film to at least one of a second electromagnetic ray and a second particle ray.

With regard to the method, it is preferred that the method further includes removing the first portion.

With regard to the method, it is preferred that the method further includes etching the substrate, such that a third portion of the substrate on which the first portion has been present is etched.

With regard to the method, it is preferred that the first electromagnetic ray of which wavelength is a first wavelength, the second electromagnetic ray of which wavelength is a second wavelength, and the first wavelength is shorter than the second wavelength.

With regard to the method, it is preferred that the first wavelength is equal to or shorter than 15 nm.

With regard to the method, it is preferred that the first wavelength is equal to or shorter than 15 nm, and the second wavelength is equal to or longer than 300 nm.

With regard to the method, it is preferred that the second exposure is carried out without a mask.

The methods are performed by using an apparatus relating to an aspect of this disclosure.

A reagent that enhances generation of a chemical species such as acid and a composition are disclosed in the disclosure. Typically, such reagent assists the generation of Brönsted acid or base from a precursor. Furthermore, such reagent can apply to the generation of Lewis acid and base. Typically, such reagent has an elimination group such as arylmethyl group, organosilyl group, organogermyl group, and organotin group and generates an intermediate such as benzyl-type radical and diarylmethyl-type radical by having a hydrogen atom abstracted.

Since such elimination group stabilizes cations, cations corresponding to benzyl-type radical and diarylmethyl-type radical are formed by the electron ejections from such radicals. Furthermore, a product having at least one double bond is formed by elimination of the elimination group. Such product has an expanded conjugation length and exhibits absorbance at a longer wavelength. Hence, such product can act as photosensitizer for a longer wavelength.

The electron ejections can be enhanced in the presence of an electron acceptor. Several photoacid generators (PAGs), which are usually contained in photoresist, can act as electron acceptor and generates by accepting an electron. Therefore, the above reagent can be utilized as acid generation enhancer (AGE) for photoresist.

Since the concept of an aspect of this disclosure can be applied to reagents that are to form polyene product, reagents can be designed in response to a wavelength of a light desired to be used for an irradiation. In other words, if such reagent is utilized as AGE for photoresist, such reagent can make freedom of processes for manufacturing devices increase.

The elimination group can act as a chemical species to deprotect a protection group. Typically, a silyl cation generated by the elimination from organosilyl compound can decompose ether and ester. Hence, deprotection of protection group can be enhanced by the elimination group, together with acid generated from PAG.

Chem. 1

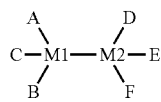
(1)

A reagent related to an aspect of the disclosure has a moiety expressed as the above structure, wherein each of M1 and M2 is element of group 14 or group 15; at least one of A, B, and C is hydrogen atom; and at least one of D, E, and F includes element of group 14 or group 15.

More concretely, it is preferred at least one of A, B, and C is an aryl group.

It is preferred that at least one of D, E, and F includes element of group 14. Typical examples of such reagent have organosilyl group, organogermyl group, or organotin group. They stabilize beta cations and are excellent elimination groups. Arylmethyl groups can be also used as an elimination group.

At least one D, E, and F can be an aryl group or include a multiple bond. For example, D, E, or F can include an aryl group or a multiple bond, such that the aryl group or the multiple bond forms expanded conjugation length, together with a multiple bond between M1 and M2 formed by elimination of at least one of A, B, and C and at least one of D, E, and F.

With regard to the reagent, it is preferred that a first elimination of C in chemical formula is capable of being occurring, and a second elimination of F in chemical formula is capable of being occurring.

It is preferred that the second elimination occurs after the first elimination.

With regard to the reagent, it is preferred that the reagent is capable of forming a multiple bond between M1 and M2 in chemical formula I through the first elimination and the second elimination.

At least one of A, B, and C has an electron-donating group. The reagent can be used as an independent molecule and as substituent bonded to a chain of polymer.

BRIEF DESCRIPTION OF THE DRAWING

In the drawings, which illustrate what is currently considered to be the best mode for carrying out the disclosure:

FIG. 1 shows fabrication processes of a device, such as an integrated circuit (IC), using photoresist including an AGE.

DETAILED DESCRIPTION

The disclosure is further described with the aid of the following illustrative Examples.

EXPERIMENTAL PROCEDURES

Synthesis of 1,1,2-tris(4-methoxyphenyl) ethene 3.14 g of triphenylphosphine is dissolved in 10 mL of toluene. 2.00 g of 4-methoxybenzyl bromide is dissolved in 10 mL of toluene and the solution of 4-methoxybenzyl bromide is added dropwise to the triphenylphosphine solution through the top of the condenser.

The mixture will warm up and a solid will precipitate. The mixture is stirred for 14 hours and the solid is removed by the filtration. Triphenyl (4-methoxyphenylmethyl) phosphonium bromide is washed with hexane.

Triphenyl (4-methoxyphenylmethyl) phosphonium bromide is dissolved in a minimum amount of water in a round bottom flask. An equal amount of toluene is added to the water as the water is poured. 2 drops of phenolphthalein solution is added into the flask. 2.5 M NaOH is added to bring the mixture to the endpoint. The toluene layer is collected and dried. 4-4-methoxybenzylidene (triphenyl) phosphorane is obtained by evaporating toluene on a rotary evaporator.

0.50 g of 4,4'-dimethoxybenzophenone is placed into a 50-mL round bottom flask equipped with a stir bar. 20 mL of dichloromethane is added and stirred for 10 minutes in an ice bath. 0.8 g of the phosphorane is slowly added. After the addition, the mixture is stirred for another 5 hours and then warmed to room temperature. 1,1,2-Tris(4-methoxyphenyl) ethene is obtained by evaporating the dichloromethane.

Synthesis of
1,1,2-tris(4-methoxyphenyl)-2-triethylsilyl-ethane
(Example)

Hydrated chloroplatinic acid (1 g) is dissolved in 2.5 ml of glacial acetic acid. The solution is diluted with 3.6 ml of water and then heated to 70 degrees Celsius. Dicyanopentadiene (1 ml) is added and the mixture is stirred for 24 hours at room temperature. The crude product is filtered and recrystallized twice from THF. It yields 0.4 g of dicyclopentadienyl platinum (II) chloride (DPPC).

In a three-necked flask, 0.2 g of Triethylhydrosilane and 0.2 g of 1,1,2-Tris(4-methoxyphenyl) ethane is dissolved in dry toluene under the protection of nitrogen. DPPC in dichloromethane is added to the mixture. The mixture is heated to reflux 50 hours. The mixture is added to methanol and the precipitate is collected. 0.08 g of 1,1,2-tris(4-methoxyphenyl)-2-triethylsilyl-ethane is obtained by drying the precipitate.

Synthesis of Resin A

A solution containing 5.0 g of alpha-methacryloyloxy-gamma-butylolactone, 6.03 g of 2-methyladamantane-2-methacrylate, and 4.34 g of 3-hydroxadamantane-1-methacrylate, 0.51 g of dimethyl-2,2'-azobis(2-methylpropionate), and 26.1 g of tetrahydrofuran is prepared. The prepared solution is added for 4 hours to 20.0 g of tetrahydrofuran placed in flask with stirring and boiling. After the addition of the prepared solution, the mixture is heated to reflux for 2 hours and cooled to room temperature. Addition of the mixture by drops to a mixed liquid containing 160 g of hexane and 18 g of tetrahydrofuran with vigorous stirring precipitates the copolymer. The copolymer is isolated by filtration. Purification of the copolymer is carried out by vacuum drying following two washings by 70 g of hexane and, thereby 8.5 g of white powder of the copolymer is obtained.

Chem. 2

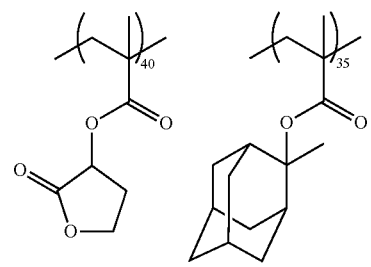

-continued

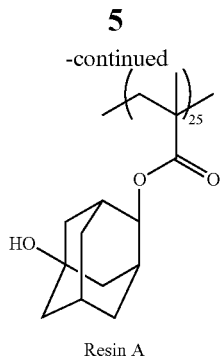

Resin A

Preparation of Samples for Evaluation (Evaluation Samples)

Evaluation Sample 1 is prepared by dissolving 300 mg of resin A, 36.7 mg of 4,4'-di-(t-butyphenyl)iodonium nonafluorobutanesulfonate as a photoacid generator, and 15.0 mg of coumarin 6 as an indicator in 2000 mg of cyclohexanone.

Evaluation Sample 2 is prepared by dissolving 6.0 mg of Example 1, 300 mg of resin A, 36.7 mg of 4,4'-di-(t-butyphenyl)iodonium nonafluorobutanesulfonate as a photoacid generator, and 15.0 mg of coumarin 6 as an indicator in 2000 mg of cyclohexanone.

Evaluation of Efficiency of Acid Generation

Each of coating films is formed on 4-inch quartz wafers by spin-coating of Evaluation Samples 1 and 2. Each of the coating films is exposed to electron beams of which volumes are 0, 10, 20, 30, and 40 microC/cm$^2$ output by an electron beam lithography apparatus. Subsequent to the electron-beam exposures, the efficiencies for each of the coating films is obtained by plotting absorbances at 534 nm, which are assigned to quantities of protonated coumarin 6 generated by the respective volumes of electron beams.

Table 1 shows the relative acid-generation efficiencies for the Evaluation Samples 1 and 2. In Table 1, the acid-generation efficiency for Evaluation Sample 1 is used as a benchmark. As shown in Table 1, the acid-generation efficiency is improved by the addition of Example 1. In other words, Example 1 functions as an Acid Generation Enhancer (AGE).

TABLE 1

The relative acid-generation efficiencies for Samples 1 and 2.

|  | Relative acid-generation efficiency |
| --- | --- |
| Evaluation Sample 1 | 1.0 |
| Evaluation Sample 2 | 1.3 |

As understood from the results, a reactive intermediate having reducing character is considered to enhance the efficiency of acid generation.

Evaluation of Sensitivity

Before applying Evaluation Sample 2 to an Si wafer, hexamethyldisilazane (HMDS, Tokyo Chemical Industry) is spin-coated at 2000 rpm for 20 seconds on the surface of the Si wafer and baked at 110 degrees Celsius for 1 minute. Then, the Evaluation Sample 2 is spin-coated on the surface of the Si wafer that has been treated with HMDS at 4000 rpm for 20 seconds to form a coating film.

The prebake of the coating film is performed at 110 degrees Celsius for 60 seconds. Then, the coating film of the Evaluation Sample 2 is exposed to electron beam (EB) output from an EB radiation source. After the EB exposure, an irradiation of the coating film with a UV light is carried out at an ambient condition. After the UV light exposure, a post-exposure-bake (PEB) is carried out at 100 degrees Celsius for 60 seconds. The coating film is developed with NMD-3 (tetra-methyl ammonium hydroxide 2.38%, Tokyo Ohka Kogyo) for 60 seconds at 25 degrees Celsius and rinsed with deionized water for 10 seconds. The thickness of the coating film measured using film thickness measurement tool is approximately 150 nm.

A sensitivity ($E_0$ sensitivity) is evaluated by measuring the doses to form a pattern constituted by 2-micrometer lines where the thickness of the coating film is not zero and 2-micrometer spaces where the thickness of the coating film is zero using 30 keV electron beam lithography (EBL) system JSM-6500F (JEOL, beam current: 12.5 pA, <1E-4 Pa) with Beam Draw (Tokyo Technology) and the UV exposures using FL-6BL (bright line is mainly from 320 nm to 380 nm, Toshiba).

Even if the UV exposure is carried out without a mask, 2-micrometer spaces are formed in the parts of the coating film that have been exposed to the EB source. This indicates that a product functioning as a photosensitizer for the UV light is generated in the parts exposed to the EB irradiation because the PAGs and the PAG moiety used for the evaluation exhibit little absorbance in a range from 320 nm to 380 nm.

TABLE 2

The doses for $E_0$ light by an EB and UV exposure for Evaluation Sample 2

|  | Total dose for $E_0$ | |
| --- | --- | --- |
|  | EB dose [μC/cm$^2$] | UV dose [mJ/cm$^2$] |
| Evaluation Sample 2 | 23 | 0 |
|  | 15 | 500 |
|  | 5 | 2000 |

Table 2 shows the dose sizes corresponding to $E_0$ sensitivities measured for the Evaluation Sample 2 containing Example 1. Table 2 indicates that the doses of the EB exposure decreases with increase of the doses of the UV light exposure.

A diarylmethyl radical is formed from Example 1 of Evaluation Sample 2 by the EB exposure and the diarylmethyl radical is oxidized to form a corresponding ethene through an elimination of triethyl silyl group. The ethane, 1,1,2-tris(4-methoxyphenyl) ethane (TA), can be excited by the UV light and function as sensitizer to enhance acid generation of the PAG. Typically, such ethane can be excited by a UV light of which wavelength is equal to or longer than 300 nm.

Further photoreaction of 1,1,2-tris(4-methoxyphenyl) ethene (TA) forms a corresponding dihydrophenanthrene (TMDHP), which is to be oxidized easily in the presence of oxygen or oxidizer to form a corresponding phenanthrene (TMPH). The phenanthrene derivative can also be used as photosensitizer. In other words, an irradiation of a longer-wavelength light can be carried out in the atmosphere.

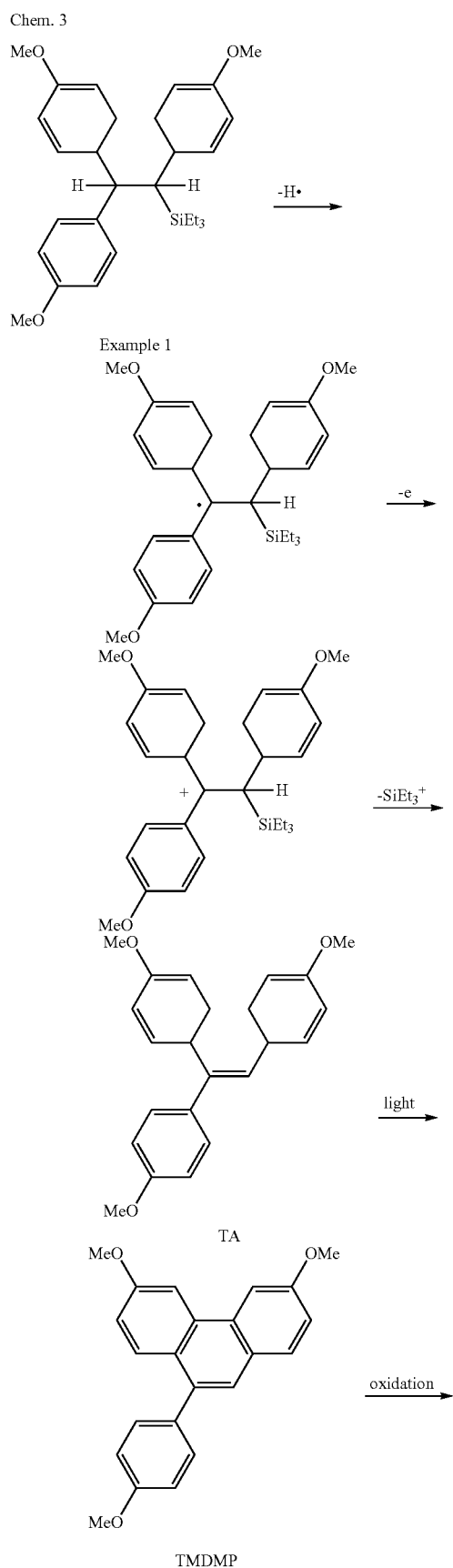

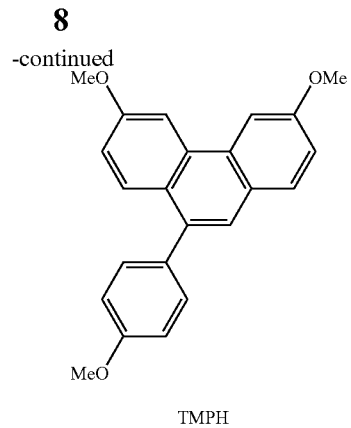

TMPH

FIG. 1 shows fabrication processes of a device, such as an integrated circuit (IC), using a photoresist including Example 1 as AGE obtained by the processes by the above procedures.

A silicon wafer is provided. The surface of the silicon wafer is oxidized by heating the silicon wafer in the presence of oxygen gas.

A solution of a chemically amplified composition (CAR) including the AGE, resin A, and a PAG is applied to the surface of an Si wafer by spin-coating to form a coating film. The coating film is prebaked.

An irradiation of the coating film with a EUV light (or an electron beam) is carried out after prebake of the Si wafer.

After the EUV irradiation of the coating film, an irradiation of the coating film with a light of which wavelength is equal to or longer than 300 nm is carried out. Such light can excite an ethene derivative generated from the AGE.

Development of the coating film is performed after the prebake. The coating film and the silicon wafer are exposed to plasma. After that, the remaining film is removed.

An electronic device such as integrated circuit is fabricated utilizing the processes shown in FIG. 1. The deterioration of the device due to the irradiation with a light is suppressed, compared to existing photoresists since times for irradiation of the coating film is shortened.

The invention claimed is:

1. A composition comprising:
   a reagent and
   a precursor,
   wherein the reagent enhances the generation of a chemical species from the Precursor;
   wherein the reagent generates an intermediate by a first exposure using a light the wavelength of which is shorter than or equal to 15 nm;
   wherein a product is formed from the intermediate by a first elimination and a second elimination;
   wherein the product is excited by a second exposure using a light of which wavelength is longer than or equal to 300 nm;
   wherein the reagent transmutes into the product acting as a photosensitizer or acts as an acid generation enhancer; and
   wherein the reagent has a moiety represented by chemical Formula (I):

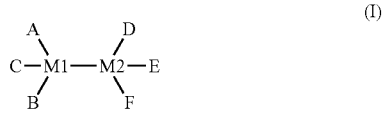

(I)

where:
- each of M1 and M2 in chemical Formula (I) is a carbon atom;
- at least one of A, B, and C in chemical Formula (I) is hydrogen and the rest of A, B, and C in chemical Formula (I) is aryl;
- at least one of D and E in chemical Formula (I) is hydrogen and the rest of D and E in chemical Formula (I) is an aryl group; and
- F is selected from the group consisting of an organosilyl group, an organogermyl group, and an organotin group.

2. The composition of claim 1, wherein at least one of the aryl groups has at least one electron-donating group.

3. A method for manufacturing a device, the method comprising:
- applying a solution of the composition of claim 1 to a substrate such that a coating film containing the composition is formed on the substrate;
- exposing the coating film to at least one of a film electromagnetic ray and a first particle ray such that a first portion of the coating film is irradiated with the at least one of the first electromagnetic ray and the first particle ray while a second portion of the coating film is not irradiated with the at least one of the first electromagnetic ray and the first particle ray; and
- exposing the coating film to at least one of a second electromagnetic ray and a second particle ray.

* * * * *